US011864985B2

(12) United States Patent
Chen et al.

(10) Patent No.: US 11,864,985 B2
(45) Date of Patent: Jan. 9, 2024

(54) ABSORBENT COMPOSITES CONTAINING EMBOSSED SUPERABSORBENT MATERIALS

(71) Applicant: Kimberly-Clark Worldwide, Inc., Neenah, WI (US)

(72) Inventors: Feng Chen, Roswell, GA (US); Wing-Chak Ng, Roswell, GA (US); Mark M. Mleziva, Appleton, WI (US)

(73) Assignee: KIMBERLY-CLARK WORLDWIDE, INC., Neenah, WI (US)

(*) Notice: Subject to any disclaimer, the term of this patent is extended or adjusted under 35 U.S.C. 154(b) by 0 days.

(21) Appl. No.: 17/917,436

(22) PCT Filed: Mar. 18, 2021

(86) PCT No.: PCT/US2021/022896
§ 371 (c)(1),
(2) Date: Oct. 6, 2022

(87) PCT Pub. No.: WO2021/221809
PCT Pub. Date: Nov. 4, 2021

(65) Prior Publication Data
US 2023/0118949 A1  Apr. 20, 2023

Related U.S. Application Data

(60) Provisional application No. 63/017,886, filed on Apr. 30, 2020.

(51) Int. Cl.
A61F 13/536 (2006.01)
A61F 13/53 (2006.01)
(Continued)

(52) U.S. Cl.
CPC ........ *A61F 13/53* (2013.01); *A61F 13/15707* (2013.01); *A61F 13/536* (2013.01); *A61L 15/60* (2013.01); *A61F 2013/530569* (2013.01); *A61F 2013/530591* (2013.01); *A61F 2013/530605* (2013.01); *A61F 2013/530635* (2013.01)

(58) Field of Classification Search
CPC ........ A61F 2013/530635; A61F 2013/530642; A61F 2013/530605; A61F 13/536
See application file for complete search history.

(56) References Cited

U.S. PATENT DOCUMENTS 6,861,477 B2    3/2005  Wang et al.
7,662,460 B2 *  2/2010  Herfert ................ A61L 15/60
                                                        604/358

(Continued)

FOREIGN PATENT DOCUMENTS

EP    1800638 A1    6/2007
EP    1637108 B1    5/2019
(Continued)

OTHER PUBLICATIONS

International Search Report and Written Opinion for Patent Application No. PCT/US2021/022896 dated Jul. 8, 2021; 10 pp.
(Continued)

Primary Examiner — Bradley H Philips
(74) Attorney, Agent, or Firm — Armstrong Teasdale LLP

(57) ABSTRACT

Described herein are absorbent composites containing embossed superabsorbent materials and methods of manufacturing absorbent composites containing embossed superabsorbent materials. The absorbent composites have significantly improved rates of intake. Compositions and methods described herein are useful in a variety of absorbent products.

17 Claims, 4 Drawing Sheets

(51) Int. Cl.
    *A61F 13/15*        (2006.01)
    *A61L 15/60*        (2006.01)

(56) References Cited

U.S. PATENT DOCUMENTS

| | | |
|---|---|---|
| 7,833,377 B2 | 11/2010 | Szypka |
| 10,065,175 B2 | 9/2018 | Lee et al. |
| 2009/0123707 A1 | 5/2009 | Skoog et al. |
| 2012/0003423 A1* | 1/2012 | Cree ............... A61F 13/512 |
| | | 428/137 |
| 2018/0243139 A1 | 8/2018 | Szypka et al. |
| 2018/0289854 A1 | 10/2018 | Varona et al. |

FOREIGN PATENT DOCUMENTS

| | | |
|---|---|---|
| EP | 1639977 B1 | 6/2019 |
| JP | 2016054755 A | 4/2016 |
| WO | 2014145312 A2 | 9/2014 |
| WO | 2015171972 A1 | 11/2015 |

OTHER PUBLICATIONS

Embossed Nonwoven Top Sheet of Sanitary Pads, Made-In-China, available at https://fixingyuan.en.made-in-china.com/product/DyCQaRYxuPWm/China-Embossed-Nonwoven-Top-Sheet-of-Sanitary-Pads.html; last visited Oct. 3, 2022; 3 pp.

* cited by examiner

ABSORBENT COMPOSITES CONTAINING EMBOSSED SUPERABSORBENT MATERIALS

CROSS-REFERENCE TO RELATED APPLICATIONS

This application claims priority to U.S. Provisional Application Ser. No. 63/017,886, filed on Apr. 30, 2020, the content of which is hereby incorporated by reference in its entirety.

FIELD OF DISCLOSURE

The present disclosure is directed to absorbent composites including embossed superabsorbent materials and methods of manufacturing absorbent composites containing embossed superabsorbent materials. The absorbent composites have significantly improved rates of intake as compared to conventional absorbent composites. Compositions and methods in accordance with the present disclosure are useful in a variety of absorbent products.

BACKGROUND

Superabsorbent materials (SAMs) are three-dimensional networks that can absorb and retain water (or other aqueous media) and physiological fluids such as urine and blood more than hundreds times of their own dry weight, typically depending on the ionic concentration of the aqueous solution. SAMs have applications in a variety of fields, including medicine, personal care products, biomaterials, biosorbents, and agriculture. SAMs were industrially developed in Japan and USA in the early 1980s for hygienic applications. It was found that SAMs had the potential to replace fluff, making their use in hygienic products such as baby diapers and feminine napkins cost effective.

Benefits of using SAM to replace fluff in absorbent products include higher absorption capacity and thinner and more flexible absorbent cores and products. One requirement of using SAM to replace fluff in an absorbent product is that SAM must have a higher absorption rate to maximize the use of available capillary spaces and compensate for the reduction of typically fast absorbing fluff fibers. It is therefore an object of the present disclosure to provide a preparation method for a SAM sheet that exhibits increased rate of water absorption that enables thinner and more flexible absorbent products.

According to previous studies, absorbent products, such as baby diapers and feminine napkins, with high SAM content (i.e. 70 wt %) leak prematurely as a result of high amount of free fluid. About 75% of leakage occurs within 90 seconds of insult. Moreover, 20 to 50% of leaks occur at the first insult and at a low load. Therefore, there is a high need for SAMs that could quickly intake fluid and reduce the amount of free fluid during absorbent product usage. Such removal of excess free fluid in absorbent products can reduce leakage and improve skin dryness.

The intake rate of SAM particles can be influenced by surface area and surface energy. Higher surface areas lead to faster intake rates. Further, faster intake rates improve the total fluid absorption by minimizing free fluid. Therefore, absorbent products with faster intake rates absorb free fluid in a more efficient way.

Methods of embossing are known to increase surface area in conventional absorbent materials. However, compressing SAM particles could damage them and reduce their effectiveness. Specifically, the high pressures applied during compression of the SAM particles can damage the mechanical properties. Compressed SAM particles could have reduced void volumes and thus reduced absorption capacities.

Described herein is a novel solution to the problem of low absorption rates in absorbent products including SAM particles. The SAM particles' surface area is increased by embossing the particles with micron sized patterns. In this way, the surface area of individual SAM particles can be increased. This embossing technique can be applied to any material including SAM particles, such as SAM sheets or flexible absorbent binder (FAB) films.

Compositions and methods in accordance with the present disclosure are useful in a variety of absorbent products, including but not limited to, personal hygiene products, wipes, bibs, wound dressings, food packaging, baby and adult diaper products, feminine pads, arm bands, agricultural and pet products that contain superabsorbent ingredients, and superabsorbent composites with fluff. The increased absorption rate can help reduce the leakage of the products; the embossment on SAM particles can also help reduce the thickness of products and increase their flexibilities.

BRIEF DESCRIPTION OF THE DISCLOSURE

In one embodiment of the present disclosure, provided herein is an absorbent composite. The absorbent composite includes a plurality of superabsorbent particles that are microembossed with an average major dimension in the range of from about 100 μm to about 1000 μm.

In another embodiment of the present disclosure, there is provided a method of manufacturing an absorbent composite. The method includes: (i) contacting a plurality of superabsorbent particles with an embossing roller comprising a plurality of pins; and (ii) embossing the plurality of superabsorbent particles with the embossing roller at a pressure in the range of from about 125 psi to about 1000 psi, wherein the plurality of superabsorbent particles are microembossed with an average major dimension in the range of from about 100 μm to about 1000 μm.

In yet another embodiment of the present disclosure, there is provided a method of manufacturing an absorbent composite. The method includes: (i) contacting a plurality of superabsorbent particles with an embossing roller comprising a plurality of pins; and (ii) transferring the plurality of superabsorbent particles to the embossing roller to emboss the plurality of superabsorbent particles directly with the plurality of pins, wherein the plurality of superabsorbent particles are microembossed with an average major dimension in the range from about 100 μm to about 1000 μm.

DETAILED DESCRIPTION OF THE DISCLOSURE

Figure 1:
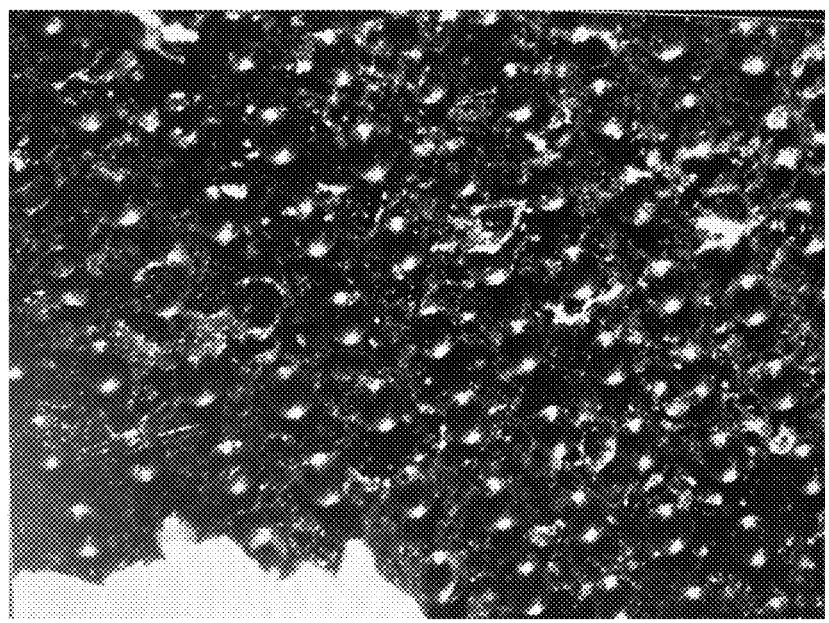
FIG. 1 is an exemplary embodiment depicting a 1"×1" metal patterned plate with protruding balls (spheres) of 250 μm diameter, the balls side facing downward towards the SAM sheet, used to produce embossed SAM and SAM-containing materials in accordance with the present disclosure.

Generally speaking, the present disclosure relates to multiple embodiments of novel absorbent composites that include a plurality of superabsorbent particles. In many embodiments, a portion or all of the superabsorbent particles are microembossed in a particular manner to increase the overall performance of the superabsorbent particles in a product, such as an absorbent product for example. The superabsorbent particles present in the absorbent composites may be in one or more various forms in accordance with the present disclosure and may be microembossed in one or more desirable patterns.

In many embodiments, absorbent composites according to the present disclosure comprise a plurality of superabsorbent particles that are microembossed with an average major dimension in the range from about 100 µm to about 1000 although other average major dimensions may also be within the scope of the present disclosure. All or only a desired portion of the superabsorbent particles may be microembossed with a desired average major dimension depending on the intended use of the superabsorbent particles. The plurality of superabsorbent particles may, in some embodiments, be in a form selected from the group consisting of free particles, a gel, a fiber, a bead, a solid, a paste, a SAM sheet, a FAB film, and combinations thereof.

In some specific embodiments of the present disclosure, the plurality of superabsorbent particles are microembossed with an average major dimension in the range from about 100 µm to about 900 µm. In some specific embodiments of the present disclosure, the plurality of superabsorbent particles are microembossed with an average major dimension in the range from about 100 µm to about 300 µm.

The plurality of superabsorbent particles can have a variety of sizes and size distributions. In some embodiments of the present disclosure, the plurality of superabsorbent particles are in a size range of from about 300-600 µm. In some embodiments of the present disclosure, the plurality of superabsorbent particles are in a size range of from about 90-300 µm. In some embodiments of the present disclosure, the plurality of superabsorbent particles are in a size range of less than about 90 µm. In some specific embodiments of the present disclosure, the plurality of superabsorbent particles is selected from the group consisting of a first plurality of superabsorbent particles in a size range of from about 300-600 µm, a second plurality of superabsorbent particles in a size range of from about 90-300 µm, a third plurality of superabsorbent particles in a size range of less than about 90 µm, and combinations thereof.

In some embodiments, the plurality of superabsorbent particles are microembossed with a pattern selected from the group consisting of a homogenous pattern and a heterogenous pattern. The pattern can comprise any geometric shape that increases surface area of the superabsorbent particles.

In some embodiments, the plurality of superabsorbent particles are microembossed with a pattern selected from the group consisting of geometric patterns, random patterns, symmetric patterns, asymmetric patterns, spheres, cubes, pyramids, and combinations thereof.

In some embodiments, the plurality of superabsorbent particles are microembossed with an average major dimension selected from a diameter, a major axis, a length, a width, and a height.

In many embodiments, a majority of the plurality of superabsorbent particles may be microembossed. In some embodiments, a majority of the plurality of superabsorbent particles means an amount greater than about 50%, greater than about 51%, greater than about 52%, greater than about 53%, greater than about 54%, greater than about 55%, greater than about 56%, greater than about 57%, greater than about 58%, greater than about 59%, greater than about 60%, greater than about 61%, greater than about 62%, greater than about 63%, greater than about 64%, greater than about 65%, greater than about 66%, greater than about 67%, greater than about 68%, greater than about 69%, greater than about 70%, greater than about 71%, greater than about 72%, greater than about 73%, greater than about 74%, greater than about 75%, greater than about 76%, greater than about 77%, greater than about 78%, greater than about 79%, greater than about 80%, greater than about 81%, greater than about 82%, greater than about 83%, greater than about 84%, greater than about 85%, greater than about 86%, greater than about 87%, greater than about 88%, greater than about 89%, greater than about 90%, greater than about 91%, greater than about 92%, greater than about 93%, greater than about 94%, greater than about 95%, greater than about 96%, greater than about 97%, greater than about 98%, greater than about 99%, or 100% of the total number of superabsorbent particles. In some specific embodiments, all of the plurality of superabsorbent particles are microembossed.

In some embodiments, the superabsorbent polymer does not comprise a crosslinker. In some embodiments, the superabsorbent polymer comprises one or more cross-linkers. In some embodiments, the superabsorbent polymer comprises two or more cross-linkers. In some embodiments, the absorbent composite comprises a crosslinker selected from the group consisting of tetraallyloxyethane, N, N'-methylene bisacryl amide, N, N'-methylene bismethacrylamide, triallylamine, trimethylol propane triacrylate, glycerol propoxy triacrylate, divinylbenzene, N-methylol acrylamide, N-methylol methacrylamide, glycidyl methacrylate, polyethylene polyamines, ethyl diamine, ethyl glycol, glycerin, tetraallyloxyethane and triallyl ethers of pentaerythritol, aluminates, silica, alumosilicates, and combinations thereof.

The amount of the crosslinking agent may vary, but is typically present in an amount of from about 0.005 to about 1.0 mole percent based on moles of the ethylenically unsaturated monomeric compound(s). In some embodiments, the crosslinking agent is present in an amount in the range of from about 0.005 mol % to about 1.0 mol %.

In some embodiments, the absorbent composite comprises a polymer comprising a monomer selected from the group consisting of 2-acrylamido-2-methylpropane sulfonic acid, methacrylate monomers with tethered sulfate groups, salts of vinyl-linker-acid units, salts of vinyl-linker-acid units, vinylic sulfate monomers, acrylic acids, vinyl sulfonic acids, vinyl phosphoric acids, partially hydrolyzed maleic anhydrides, carboxymethylcellulose, sodium alginate, chitosan salt, modified starches, modified soy protein, and combinations thereof.

In some embodiments, the absorbent composite is used in a consumer product. In some embodiments, a consumer product comprises the absorbent composite.

In some embodiments, a method of using an absorbent composite in accordance with the present disclosure comprises using the absorbent composite in a consumer product.

In some embodiments, the consumer product is selected from the group consisting of cloth products, wipes, napkins, bibs, disposable bed liners, wound dressings, food packaging, baby and adult diaper products, feminine pads, arm bands, agricultural and pet products, and combinations thereof.

Absorbent composites according to the present disclosure may be processed and/or manufactured according to any suitable methods. In one specific embodiment, a method may comprise contacting a plurality of superabsorbent particles with an embossing roller comprising a plurality of pins, and embossing the plurality of superabsorbent particles with the embossing roller at a pressure in the range from about 125 psi to about 1000 psi. In this method, the plurality of superabsorbent particles are microembossed with an average major dimension in the range from about 100 µm to about 1000 µm. The superabsorbent particles can further be combined with a composite material, such as fluff, to form a superabsorbent composite.

Absorbent composites according to the present disclosure may also be manufactured according to a method comprising contacting a plurality of superabsorbent particles with an embossing roller comprising a plurality of pins and transferring the plurality of superabsorbent particles to the embossing roller to emboss the plurality of superabsorbent particles directly with the plurality of pins. In this method, the plurality of superabsorbent particles are microembossed with an average major dimension in the range from about 100 µm to about 1000 µm. The superabsorbent particles can further be combined with a composite material, such as fluff, to form a superabsorbent composite.

The above-described methods for manufacturing the absorbent composites of the present disclosure may include the use of one or more heating cycles during the embossing steps. In some embodiments, the above-described methods according to the present disclosure comprise an embossing step that is substantially or completely free of applied heat. In other embodiments, applied heat may be used in some embossing steps but not in others.

EXAMPLES

Without further elaboration, it is believed that one skilled in the art using the preceding description can utilize the present invention to its fullest extent. The following Examples are, therefore, to be construed as merely illustrative, and not limiting of the disclosure in any way whatsoever.

SAM Sheet Preparation.

Due to the rigidity of individual SAM particles, it is very difficult to re-shape the SAM particles with surface cross-linking. Therefore, plasticization and softening of these SAM particles is required. $H_2O$ moisture, in this case, is applied as plasticizer to the SAM particles. Other plasticizers, i.e. glycerol or other polymers with small molecular weight, can also be used to soften SAM particles.

The SAM used in the SAM sheets of the examples of this disclosure is SG200. SG200 is a white odorless free-flowing powder having the ability to absorb solutions. It is a cross-linked and partially neutralized acrylic acid polymer sodium salt that has been classified to reduce dust and chemically treated to prevent caking. 9% of the particles are larger than 600 µm, 70% of the particles are within the size range of from about 300-600 µm, 20.5% of the particles are within the size range of from about 90-300 µm, and 0.5% of the particles are smaller than 90 µm. The apparent density of SG200 is 0.61 g/cc. It has residual monomer amount of about 60 ppm.

10 grams of superabsorbent particles (SG200) was spread out on bell glass and placed in a humidity chamber with 80% relative humidity (RH) for 12 hours. The SAM particles became soft and spongy after the humidity treatment. 2 g of plasticized SAM were weighed and spread between two flat metal sheets in an attentive way that no interstices between the particles existed. A Carver automatic hydraulic compressor (CE, Model 4350) applied an 18000 lb load for 5 minutes to compress the SAM particles into thin SAM sheets. The resultant SAM sheets were quite elastic with opaque color. Two SAM sheets were prepared for control and compression embossing, respectively.

Comparative Example 1. SAM Sheet without Embossing

A 1 g compressed SAM sheet was formed without embossing. To ensure that Comparative Example 1 had the same compactness as Example 1, meaning that both samples experienced the same compressing pressure, the SAM sheets were each placed between two flat metal plates and compressed twice with a 1000 lb load for 10 minutes using the Carver hydraulic compressor (CE, Model 4350). In this way, the void volumes between and within SAM particles are quite close, if not the same, for Comparative Example 1 and Example 1. The sample was dried in a convection oven at 80° C. for 12 hours before testing.

Example 1. SAM Sheet with Embossing

Figure 2:
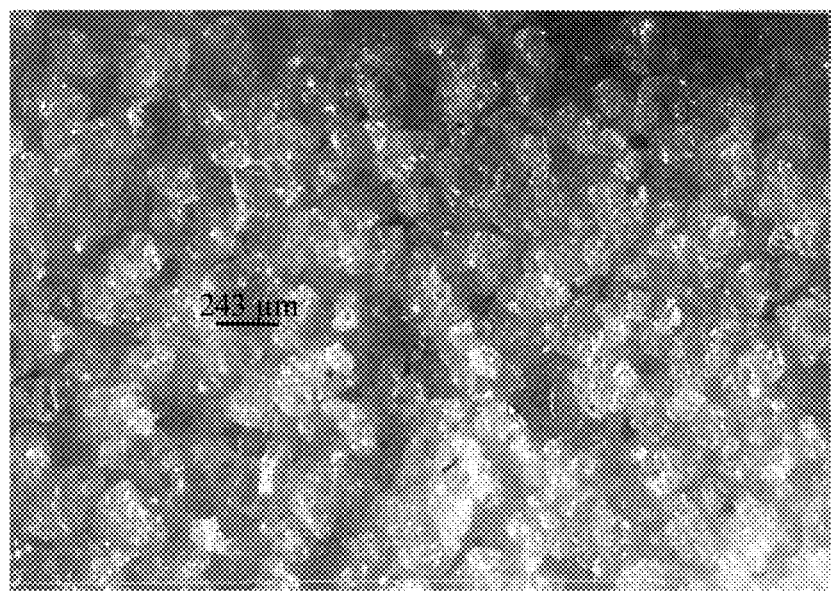
FIG. 2 is an exemplary embodiment depicting a SAM sheet with an embossed pattern on the surface in accordance with the present disclosure.

A 1 g compressed SAM sheet was formed without embossing. The prepared SAM sheet was placed on a flat metal plate, covered with a 1"×1" metal patterned plate with protruding balls of 250 µm diameter, the balls side facing downward towards the SAM sheet (FIG. 1). The Carver hydraulic compressor (CE, Model 4350) was used to create the embossing pattern by applying a 1000 lb load to a plasticized SAM sheet for 5 minutes. After that, the SAM sheet was flipped over and compressed one more time with the metal balls under same pressure and same dwell time. The resultant SAM sheet has a clear pattern on the surface (FIG. 2). The scale bar shows the diameter of dent of 243 µm. The size of the dent is consistent with the size of metal balls of the embossing plate.

The final 1 g compressed SAM sheet had two-sided embossing. The sample was dried in a convection oven at 80° C. for 12 hours before testing.

The protrusions of this example were ball-shaped, but the protrusion of the pins could be any shape. Shapes without sharper corners, such as spheres, could be less damaging to the SAM particles. The depth of the indentations from the shapes could be in the range of from about 10 µm to 200

Absorbency Evaluation.

Equal masses of embossed and non-embossed SAM sheet samples were each individually dropped in a 100 mL beaker containing 30 mL NaCl solution, which contained blue dye to improve visualization during testing. The time and process of the SAM sheet completely absorbing the saline solution was monitored and compared.

Figure 3:
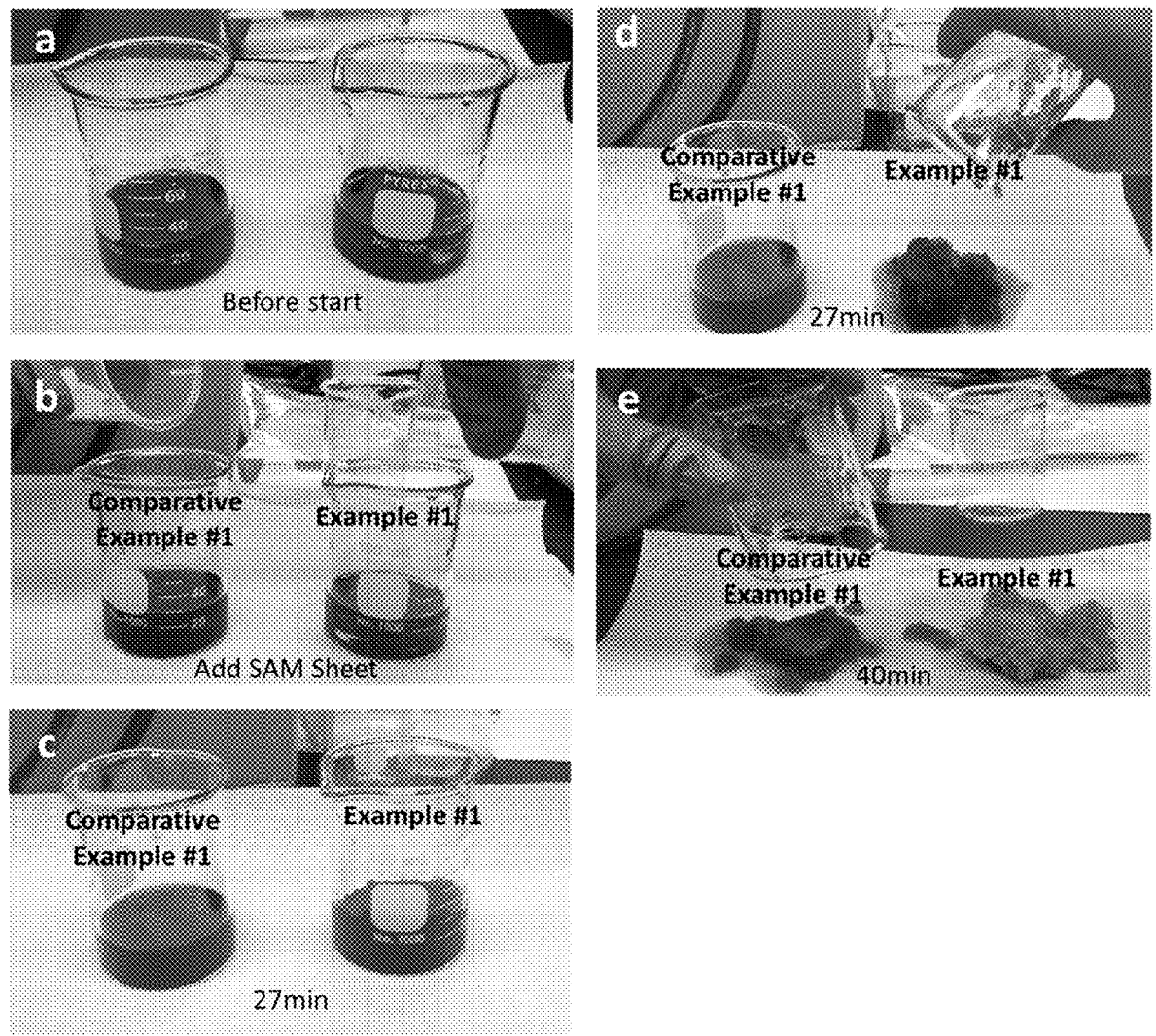
FIG. 3a shows testing beakers with 30 mL NaCl solution and blue dye in an exemplary embodiment depicting the testing process to compare the absorbency properties of non-embossed SAM sheet samples and embossed SAM sheet samples in accordance with the present disclosure.
FIG. 3b shows at the start of the testing (0 min) by adding SAM sheets into the respective NaCl solutions in an exemplary embodiment depicting the testing process to compare the absorbency properties of non-embossed SAM sheet samples and embossed SAM sheet samples in accordance with the present disclosure.
FIG. 3c shows the completion of absorption of liquid for the embossed sample at 27 minutes in an exemplary embodiment depicting the testing process to compare the absorbency properties of non-embossed SAM sheet samples and embossed SAM sheet samples in accordance with the present disclosure.
FIG. 3d shows that the swollen embossed SAM particles were cast off onto white paper to verify the complete absorption of the fluid in an exemplary embodiment depicting the testing process to compare the absorbency properties of non-embossed SAM sheet samples and embossed SAM sheet samples in accordance with the present disclosure.
FIG. 3e shows that the swollen non-embossed SAM particles were cast off onto white paper to verify the complete absorption of the fluid in an exemplary embodiment depicting the testing process to compare the absorbency properties of non-embossed SAM sheet samples and embossed SAM sheet samples in accordance with the present disclosure

The testing process for both samples to compare their absorbency properties is shown in FIGS. 3a-3e. FIG. 3a shows the testing beakers with 30 mL NaCl solution and blue dye. FIG. 3b shows at the start of the testing (0 min) by adding SAM sheets into the respective NaCl solutions. FIG. 3c shows the completion of absorption of liquid for Example 1 at 27 minutes. After completion, the swollen SAM particles were cast off onto white paper to verify the complete absorption of the fluid (FIG. 3d). At 40 min, Comparative Example 1 completed absorbing all fluid and was cast off onto white paper to verify completion (FIG. 3e). By the time Comparative Example 1 was cast off onto white paper, Example 1 had already turned white because it had finished the absorbing process 13 minutes earlier and the absorbed fluid already diffused into the center of each SAM particle. Absorbency times are summarized in Table 1.

TABLE 1

Absorbency times for SAM sheets.

| Sample | Intake time (min) |
|---|---|
| Comparative Example 1 | 40 |
| Example 1 | 27 |

Compressing SAM particles into sheets generally leads to lower intake rates and higher intake times compared with SAM particles that are not compressed into sheets due to the loss of free volume within SAM molecular structure and surface area. However, the results demonstrated herein prove that SAM with surface embossing could lead to increase of surface area, thereby increasing the absorbency intake rate compared to the compressed SAM without embossing.

Flexible Absorbent Binder Film.

FAB is a proprietary crosslinked acrylic acid copolymer that develops absorbency properties after it is applied to a substrate and dried, FAB itself can also be casted into film and dried, yet the resultant 100% FAB film is quite rigid and stiff. The chemistry of FAB is similar to standard SAPs except that the latent crosslinking component allows it to be applied onto the substrate of choice as an aqueous solution and then converted into a superabsorbent coating upon drying. When the water is removed, the crosslinker molecules in the polymeric chain come into contact with each other and covalently bond to form a crosslinked absorbent.

In the examples of this disclosure, FAB was coated on a nonwoven substrate to provide a single layer with both intake and retention functions, as well as flexibility. FAB solution with 32% (wt/wt) solids was coated on a nonwoven substrate through a slot die with two rolls. After coating, the coated film was cured by drying in a convection oven at 55° C. for 20-30 minutes, or until the film was dry, to remove the water.

Compression embossing was applied on FAB films. Two-sided embossing was applied on a FAB film. The absorbent properties were characterized and compared through saline absorption testing. The FAB film with an embossed pattern showed 91.67% faster intake rate compared with the FAB film without an embossed pattern.

Comparative Example 2. FAB Film without Embossing

An FAB film was formed without embossing. The sample was dried in a convection oven at 80° C. for 4 hours before testing.

Example 2. FAB Film with Embossing

An FAB film was formed without embossing. The film was placed on a flat metal plate and then covered with 12"×12" metal patterned plate with protruded 1 mm×1 mm square pins (each with a height of 0.5 mm), with the pins' side facing downward towards the FAB film. The plates, and the FAB film between them, were placed in between the plates of a Carver automatic hydraulic compressor. An 18000 lb load was applied for 1.5 minutes to emboss the FAB film. After that, the FAB film was flipped over and compressed one more time with the metal pins under same pressure and same dwell time.

An average major dimension of the pins was in the range of from about 100 µm to about 100 µm. The indentation from each pin was in the range of from about 10 µm to about 200 µm.

The final FAB film had two-side embossing. The sample was dried in a convection oven at 80° C. for 4 hours before testing.

Absorbency Evaluation.

Equal masses of embossed and non-embossed FAB film samples were each individually placed in a bell glass. 1 mL NaCl solution was placed on top of each sample by a pipette.

The solutions also contained blue dye to improve visualization during testing. The time started once the 1 mL NaCl solutions were dropped on the respective samples. The time of the samples absorbing the saline solution was monitored and the absorption behavior was observed. The difference of the absorbency was characterized qualitatively.

Figure 4:
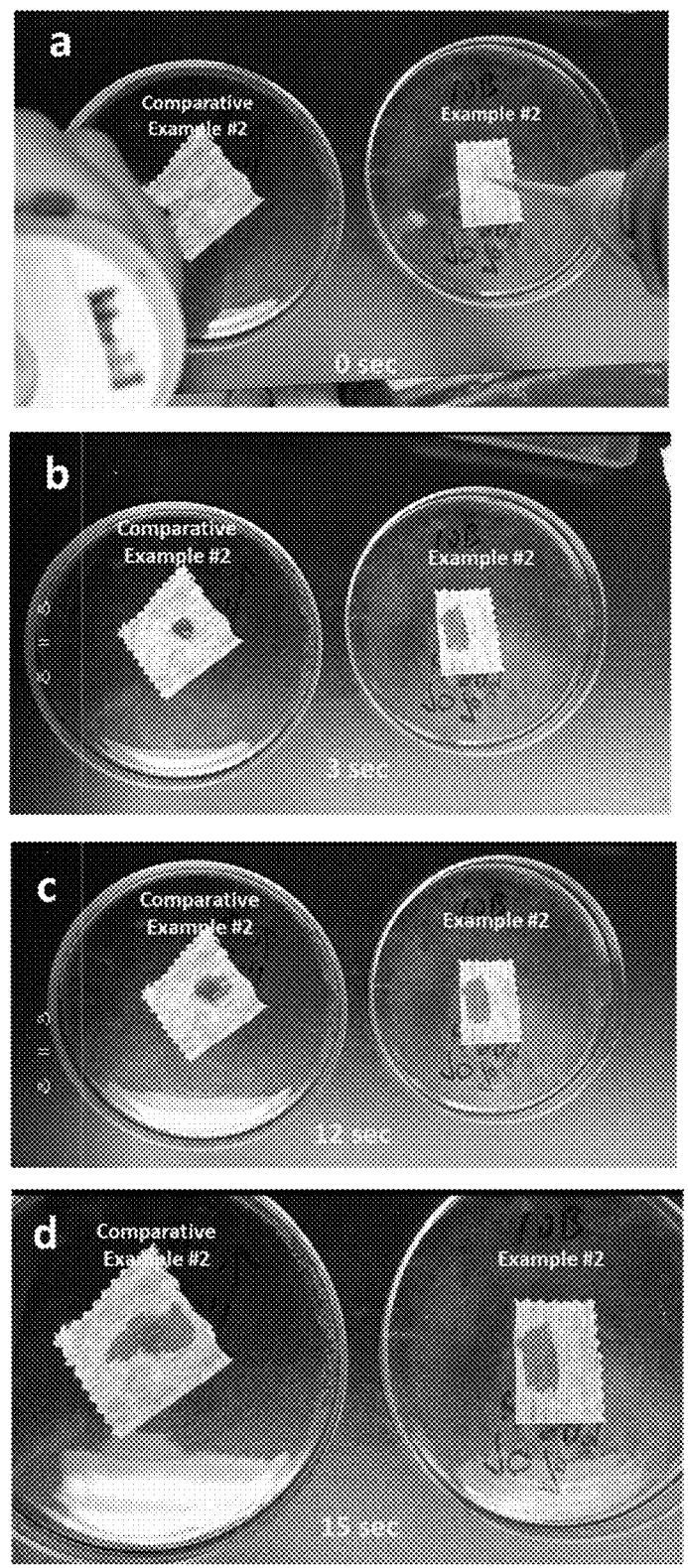
FIG. 4a shows the start of the test (0 seconds) in an exemplary embodiment depicting the testing process to compare the absorbency properties of non-embossed FAB film samples and embossed FAB film samples in accordance with the present disclosure.
FIG. 4b shows that once the NaCl solution was dropped onto each film sample, the embossed sample demonstrated an immediate absorption of the liquid and distributed it into all directions within the film in an exemplary embodiment depicting the testing process to compare the absorbency properties of non-embossed FAB film samples and embossed FAB film samples in accordance with the present disclosure.
FIG. 4c shows that starting at 12 seconds, the non-embossed sample demonstrated an intake behavior for the fluid and started to distribute the liquid into all directions within the film in an exemplary embodiment depicting the testing process to compare the absorbency properties of non-embossed FAB film samples and embossed FAB film samples in accordance with the present disclosure.
FIG. 4d shows that at 15 seconds, it can still be seen that for the non-embossed sample, the central intake area has a higher fluid amount compared with the surrounding area in an exemplary embodiment depicting the testing process to compare the absorbency properties of non-embossed FAB film samples and embossed FAB film samples in accordance with the present disclosure.

FIGS. 4a-4d shows the testing process of both samples to compare their absorbency properties. FIG. 4a shows the start of the test (0 seconds). Once the NaCl solution was dropped onto each film sample, Example 2 demonstrated an immediate absorption of the liquid and distributed it into all directions within the film (FIG. 4b). This observation indicates a more hydrophilic surface, potentially from a lower contact angle, compared with Comparative Example 2. Such rapid absorption is beneficial for fluid absorption. Starting at 12 seconds, Comparative Example 2 showed an intake behavior for the fluid and started to distribute the liquid into all directions within the film (FIG. 4c). At 15 seconds in FIG. 4d, it can still be seen that for Comparative Example 2, the central intake area has a higher fluid amount compared with the surrounding area. This observation indicates that the fluid distribution of the non-embossed FAB film is not as even as that for the embossed FAB film. Absorbency times are summarized in Table 2.

TABLE 2

Absorbency times for FAB films.

| Sample | Intake time (sec) |
|---|---|
| Comparative Example 2 | 12 |
| Example 2 | 1 |

One possible reason for the improved distribution and relatively higher absorption properties for Example 2 could be the reduction of surface tension effected by the embossing treatment, which also causes the reduction of contact angle, thereby increasing the osmotic pressure to improve the intake behavior of SAM.

This written description uses examples to illustrate the present disclosure, including the best mode, and also to enable any person skilled in the art to practice the disclosure, including making and using any compositions or systems and performing any incorporated methods. The patentable scope of the disclosure is defined by the claims, and may include other examples that occur to those skilled in the art. Such other examples are intended to be within the scope of the claims if they have elements that do not differ from the literal language of the claims, or if they include equivalent elements with insubstantial differences from the literal language of the claims.

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where an invention or a portion thereof is defined with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As used herein, the term "about" means plus or minus 10% of the value.

What is claimed is:

1. An absorbent composite comprising:
   a plurality of superabsorbent particles;
   wherein the plurality of superabsorbent particles are microembossed with an average major dimension in the range of from about 100 μm to about 300 μm.

2. The absorbent composite of claim 1, wherein the plurality of superabsorbent particles form an SAM sheet.

3. The absorbent composite of claim 1, wherein the plurality of superabsorbent particles are microembossed with a pattern selected from the group consisting of a homogenous pattern and a heterogenous pattern.

4. The absorbent composite of claim 1, wherein the plurality of superabsorbent particles are microembossed with a pattern selected from the group consisting of geometric patterns, random patterns, symmetric patterns, asymmetric patterns, spheres, cubes, pyramids, and combinations thereof.

5. A consumer product comprising the absorbent composite of claim 1, wherein the consumer product is selected from the group consisting of personal hygiene product, wipes, bibs, wound dressings, napkins, disposable bed liners, food packaging, baby and adult diaper products, feminine pads, arm bands, agricultural and pet products that contain superabsorbent ingredients, superabsorbent composites comprising fluff, and combinations thereof.

6. A method of manufacturing an absorbent composite, the method comprising:
   contacting a plurality of superabsorbent particles with an embossing roller comprising a plurality of pins; and
   embossing the plurality of superabsorbent particles with the embossing roller at a pressure in the range from about 125 psi to about 1000 psi;

wherein the plurality of superabsorbent particles are microembossed with an average major dimension in the range of from about 100 μm to about 300 μm.

7. The method of claim 6, wherein the plurality of superabsorbent particles form an SAM sheet.

8. The method of claim 6, wherein the plurality of superabsorbent particles are microembossed with a pattern selected from the group consisting of a homogenous pattern and a heterogenous pattern.

9. The method of claim 6, wherein the plurality of superabsorbent particles are microembossed with a pattern selected from the group consisting of geometric patterns, random patterns, symmetric patterns, asymmetric patterns, spheres, cubes, pyramids, and combinations thereof.

10. The method of claim 6, wherein the embossing step is free of applied heat.

11. A consumer product comprising the absorbent composite manufactured according to claim 6, wherein the consumer product is selected from the group consisting of personal hygiene product, wipes, bibs, wound dressings, napkins, disposable bed liners, food packaging, baby and adult diaper products, feminine pads, arm bands, agricultural and pet products that contain superabsorbent ingredients, superabsorbent composites comprising fluff, and combinations thereof.

12. A method of manufacturing an absorbent composite, the method comprising:
    contacting a plurality of superabsorbent particles with an embossing roller comprising a plurality of pins; and
    transferring the plurality of superabsorbent particles to the embossing roller to emboss the plurality of superabsorbent particles directly with the plurality of pins;
    wherein the plurality of superabsorbent particles are microembossed with an average major dimension in the range from about 100 μm to about 300 μm.

13. The method of claim 12, wherein the plurality of superabsorbent particles form an SAM sheet.

14. The method of claim 12, wherein the plurality of superabsorbent particles are microembossed with a pattern selected from the group consisting of a homogenous pattern and a heterogenous pattern.

15. The method of claim 12, wherein the plurality of superabsorbent particles are microembossed with a pattern selected from the group consisting of geometric patterns, random patterns, symmetric patterns, asymmetric patterns, spheres, cubes, pyramids, and combinations thereof.

16. The method of claim 12, wherein the embossing step is free of applied heat.

17. A consumer product comprising the absorbent composite manufactured according to claim 12, wherein the consumer product is selected from the group consisting of personal hygiene product, wipes, bibs, wound dressings, napkins, disposable bed liners, food packaging, baby and adult diaper products, feminine pads, arm bands, agricultural and pet products that contain superabsorbent ingredients, superabsorbent composites comprising fluff, and combinations thereof.

* * * * *